United States Patent
Gevers et al.

(10) Patent No.: US 11,331,593 B2
(45) Date of Patent: May 17, 2022

(54) UREA PLANT WITH STRIPPER AND STRIPPING METHOD

(71) Applicant: STAMICARBON B.V., Sittard (NL)

(72) Inventors: Lambertus Wilhelmus Gevers, Merkelbeek (NL); Juan Coloma González, Maastricht (NL)

(73) Assignee: STAMICARBON B.V., Sittard (NL)

( * ) Notice: Subject to any disclaimer, the term of this patent is extended or adjusted under 35 U.S.C. 154(b) by 0 days.

(21) Appl. No.: 17/423,139

(22) PCT Filed: Jun. 5, 2020

(86) PCT No.: PCT/NL2020/050364
§ 371 (c)(1),
(2) Date: Jul. 15, 2021

(87) PCT Pub. No.: WO2020/246886
PCT Pub. Date: Dec. 10, 2020

(65) Prior Publication Data
US 2022/0040591 A1    Feb. 10, 2022

(30) Foreign Application Priority Data

Jun. 7, 2019  (EP) .................................... 19179019

(51) Int. Cl.
B01D 1/06   (2006.01)
B01D 1/28   (2006.01)
(Continued)

(52) U.S. Cl.
CPC .......... *B01D 1/065* (2013.01); *B01D 1/2887* (2013.01); *B01D 19/0015* (2013.01); *C07C 273/189* (2013.01); *C07C 273/04* (2013.01)

(58) Field of Classification Search
CPC .. B01D 1/065; B01D 1/2887; B01D 19/0015; C07C 273/189; C07C 273/04
See application file for complete search history.

(56) References Cited

U.S. PATENT DOCUMENTS 3,957,868 A * 5/1976 Verstegen ............. C07C 273/04
564/71
4,486,270 A * 12/1984 Kaasenbrood ........ C07C 273/04
165/111
(Continued)

FOREIGN PATENT DOCUMENTS

EP    1195194 A1    4/2002
EP    1375475 A1    1/2004
(Continued)

OTHER PUBLICATIONS

Wainwright, editor. "Acron to Expand Production of Nitric Acid in Veliky Novgorod." World Fertilizer Magazine, Jan./Feb. 2019, www.worldfertilizer.com. 1 page.
(Continued)

*Primary Examiner* — Jonathan Miller
(74) *Attorney, Agent, or Firm* — Leason Ellis LLP (57) ABSTRACT

A method is disclosed for stripping in a stripper a urea synthesis solution received from a urea forming process wherein ammonia and CO2 are reacted under urea forming conditions. The shell space of the stripper comprises a continuous vertical zone.

20 Claims, 2 Drawing Sheets

(51) Int. Cl.
  *B01D 19/00*  (2006.01)
  *C07C 273/18*  (2006.01)
  C07C 273/04  (2006.01)

(56) References Cited

U.S. PATENT DOCUMENTS

| | | | |
|---|---|---|---|
| 4,579,304 A * | 4/1986 | Williams | F28F 9/0136 |
| | | | 165/172 |
| 9,068,781 B2 * | 6/2015 | Gianazza | B01D 1/065 |
| 10,604,477 B2 * | 3/2020 | Sato | B01J 19/0053 |
| 2012/0097378 A1 | 4/2012 | Gianazza et al. | |
| 2012/0282149 A1 | 11/2012 | Mennen et al. | |

FOREIGN PATENT DOCUMENTS

| | | |
|---|---|---|
| WO | 9500674 A1 | 1/1995 |
| WO | 2005090893 A1 | 9/2005 |
| WO | 2017013180 A1 | 1/2017 |
| WO | 2017014632 A1 | 1/2017 |

OTHER PUBLICATIONS

International Search Report and Written Opinion in corresponding International Patent Application No. PCT/NL2020/050364 dated Sep. 18, 2020. 11 pages.
Australian Examination Report in corresponding Australian Patent Application No. 2020288071 dated Jun. 8, 2021. 9 pages.
No Author. "Safurex Precision Resilience." Advertisement in World Fertilizer Magazine, Jan./Feb. 2019, www.worldfertilizer.com. 1 page.

* cited by examiner

UREA PLANT WITH STRIPPER AND STRIPPING METHOD

CROSS-REFERENCE TO RELATED PATENT APPLICATIONS

This application is a U.S. National Stage Application under 35 U.S.C. § 371 of International Patent Application No. PCT/NL2020/050364 filed Jun. 5, 2020, which claims the benefit of priority of European Patent Application numbers 19179019.5 filed Jun. 7, 2019, both of which are incorporated by reference in their entireties. The International Application was published on Dec. 10, 2020, as International Publication No. WO 2020/246886 A1.

FIELD

The invention pertains to method for stripping a urea synthesis solution and to a urea plant. The invention also pertains to a shell-and-tube heat exchanger, a stripper for a urea plant, a urea production process and a method of modifying a urea plant. The invention further pertains to a method of modifying a urea plant.

INTRODUCTION

Urea plants according to the striping process design comprise a high pressure (HP) stripper which is a shell-and-tube heat exchanger comprising a vertical tube bundle, a shell, and a shell space between the shell and the tubes. The stripper is configured as falling film heat exchanger for receiving urea synthesis solution to be stripped in the tubes and for receiving a condensable heating fluid in the shell space. The shell comprises an inlet for condensable gaseous heating fluid, such as steam, as well as an outlet for condensate. A large part of the steam condenses in the shell space. For instance at least 15 kg/hr or e.g. 20-40 kg/hr steam condensate per tube is withdrawn from the stripper in operation.

The urea synthesis solution comprises, besides urea, ammonium carbamate and water and typically free ammonia and $CO_2$. The ammonium carbamate is extremely corrosive at the usual temperatures in the stripper (e.g. above 150° C., for instance in the range 180° C.-220° C.). Hence the stripper tubes are typically made of special steel grades, such as duplex austenitic-ferritic stainless steel. Example steel grades are described in WO 95/00674, WO 2017/013180 and WO 2017/014632.

Although generally good corrosion resistance and long lifetime of the stripper tubes is achieved with these kinds of steel, certain corrosion may still occur. In particular for an example single train urea plant with a design capacity of e.g. at least 2700 MTPD (metric ton per day) urea, the stripper may comprise for instance a tube bundle having 3500 to 6000 tubes giving a tube bundle diameter of about 3.0 to 3.5 m. Tube bundles with even more tubes are possible. It is found that for very large tube bundles, there is some risk of corrosion.

Corrosion of the stripper tubes is dependent on temperatures in the tubes. Corrosion has been observed to occur predominantly in certain vertical parts of the tube as a result of a temperature profile over the tubes from bottom to top. Maximum corrosion of the tubes is for instance observed in a vertical zone at 70-90% of the effective tube length from the top of the effective tube length. In the higher parts of the tubes, the temperature of the urea solution is still relatively low and increases from the top to the bottom. In the lowest part of the effective tube length, the concentration of ammonium carbamate is low.

Generally for shell-and-tube heat exchangers, it is customary that baffles are installed on the shell side to give a higher heat-transfer rate due to increased turbulence and to support the tubes thus reducing the chance of damage due to vibration. Also in strippers of urea plants, usually baffles are placed in the shell space in order to improve heat exchange between the steam and the tubes by ensuring a desired flow pattern of steam in the shell space. For example World Fertilizer Magazine February 2019 page 8 schematically shows a design of a HP stripper of a urea plant with disc-and-donut baffles.

Example types of baffle arrangements includes single segmental, double segmental, and disc-and-donut. These types of baffles are baffle plates with holes for the tubes. The baffle plates leave some open space in the shell space in horizontal cross section at the height of the baffles to allow for flow of the heating fluid along the baffle. The center-to-center distance between baffles is called the baffle-pitch and this can be adjusted to vary the crossflow velocity. In practice, the baffle pitch is normally smaller than some maximum baffle pitch which is usually much smaller than the inside diameter of the shell. With appropriate baffle pitch, segmental baffles serve not only for directing flow in the shell space, but also protect the tubes from damage by vibration and prevent the tubes from buckling.

Segmental baffles, disc baffles and donut baffles and other kinds of baffles are typically metal plates comprising holes for the tubes. The tubes typically fit in the holes without significant clearance, e.g. no clearance of more than 2.0 mm typically no more than 0.5 mm, for example 0.2 mm. Hence, the tube holes in the baffle plates typically do not allow for significant drainage of condensate.

An object of the present invention is to provide a high pressure stripper for a urea plant that addresses the above-mentioned problems of tube corrosion of the stripper tubes at least in part; as well as a urea plant comprising such stripper and a method of stripping urea solution using such a stripper. Further objectives are discussed in the following description.

SUMMARY

The invention relates in a first aspect to a method for stripping a urea synthesis solution received from a urea forming process wherein ammonia and $CO_2$ are reacted under urea forming conditions, wherein the urea synthesis solution comprises urea, water and ammonium carbamate, the method comprising:

subjecting the urea synthesis solution to stripping and indirect heat exchange with a gaseous heating fluid in a stripper, wherein the stripper is a vertical shell-and-tube heat exchanger comprising a tube bundle comprising tubes, a shell and a shell space, wherein the urea synthesis solution is provided as falling film in the tubes and wherein the heating fluid is supplied in the shell space and condenses at least in part in the shell space, wherein the tube bundle preferably has an effective tube length of 4 to 9 m, wherein the effective tube length is the length of the tube part that is in contact with the heating fluid, wherein the tube bundle has an outer tube limit and preferably a ratio of the effective tube length to the outer tube limit diameter that is 2.5 or less, wherein the outer tube limit is the diameter of the circle created by encircling the outermost tubes in the tube bundle, wherein the shell space preferably has at each vertical level a drainage area for heating fluid condensate, wherein said shell space preferably comprises a continuous vertical zone of at least 1.6 m vertical length, wherein said continuous vertical zone does not include baffles (and preferably does not include segmental baffles, disc baffles or donut baffles) and/or wherein in said continuous vertical zone for each horizontal cross section of said shell space in said vertical zone, the difference in drainage area for heating fluid condensate between any two circular areas of at least 0.25 m$^2$ which have the same size and which are located in a region in said horizontal cross section and within said outer tube limit is less than 5% relative to the average drainage area of the two circular areas; and/or wherein said continuous vertical zone does not include baffles.

The invention relates in a further aspect to a method for stripping a urea synthesis solution received from a urea forming process wherein ammonia and $CO_2$ are reacted under urea forming conditions, wherein the urea synthesis solution comprises urea, water and ammonium carbamate, the method comprising:

subjecting the urea synthesis solution to stripping and indirect heat exchange with a gaseous heating fluid in a stripper, wherein the stripper is a vertical shell-and-tube heat exchanger comprising a tube bundle comprising tubes, a shell and a shell space, wherein the urea synthesis solution is provided as falling film in the tubes and wherein the heating fluid is supplied in the shell space and condenses at least in part in the shell space, wherein the tube bundle preferably has an effective tube length of 4 to 9 m, wherein the effective tube length is the length of the tube part that is in contact with the heating fluid, wherein the shell space preferably has, at each vertical level where the tubes are contacted with heating fluid, a drainage area for heating fluid condensate, and wherein tubes are supported by strips, wherein the strips preferably have a width of less than 10 mm.

The invention pertains also to such strippers as used or as defined in said methods.

The invention also pertains to a urea plant comprising a high pressure synthesis section comprising a urea reaction section, a high pressure carbamate condenser and a stripper, wherein the stripper is configured as vertical falling film shell-and-tube heat exchanger and comprises a tube bundle comprising tubes, a shell, and an upper tube sheet and lower tube sheet, and a shell space provided in the shell between the upper and lower tube sheet, wherein the stripper is adapted for maintaining a falling film of urea synthesis solution to be stripped in the tubes and comprises an inlet for gaseous heating fluid supplied to the shell space and an outlet for gaseous heating fluid and heating fluid condensate from the shell space, wherein the tube bundle preferably has an effective tube length of 4 to 9 m, wherein the effective tube length is the length of the tube part that is in operation in contact with the heating fluid, wherein the tube bundle has an outer tube limit and preferably a ratio of the effective tube length to the outer tube limit diameter that is 2.5 or less, wherein the outer tube limit is diameter of the circle created by encircling the outermost tubes in the tube bundle, wherein the shell space preferably has, at each vertical level where the tubes are contacted with the heating fluid, a drainage area for heating fluid condensate, wherein said shell space preferably (1) comprises a continuous vertical zone of at least 1.6 m vertical length wherein for each horizontal cross section of said shell space in said vertical zone, the difference in drainage area between any two circular areas of at least 0.25 m$^2$ which have the same size and which are located in said horizontal cross section within said outer tube limit is less than 5% relative to the average drainage area of the two circular areas, and/or (2) wherein said continuous vertical zone does not include baffles, wherein the tubes are (3) preferably supported by strips, wherein the strips preferably have a width of less than 10 mm. The invention also pertains to such a stripper. The stripper e.g. has said feature (1), or said feature (2), or feature (3), such as feature (1) and (2) in combination, or feature (2) and (3) in combination, or features (1), (2) and (3) in combination. The same applies for the stripper used in the method.

DETAILED DESCRIPTION

The invention is based on the judicious insight that the corrosion of stripper tubes in high pressure stripers of urea plants can be reduced by avoiding the accumulation of heating fluid condensate (e.g. steam condensate) in the shell space of the stripper near the tubes at the vertical zones of the tubes where tubes are at risk of corrosion. Such accumulation of condensate in the shell space may in particular occur when the tube bundle diameter is large and accordingly the conventionally used baffles (e.g. segmental baffles or disc and donut baffles) are large as well, such that condensate is not or not sufficiently removed by drainage. The present inventors surprisingly found that by preventing such accumulation of condensate, local heat exchange efficiency is improved in zones of the stripper that are at risk of condensate accumulation. This better local heat exchange efficiency improves the overall heat exchange efficiency of the stripper, resulting in a higher stripping efficiency (alfa). Accordingly, to achieve a given fixed stripping efficiency (alfa) the temperature, and consequently pressure, of the steam in the shell-side of the stripper can be lower than in case of condensate accumulation. A higher shell side steam temperature, and consequently pressure (to compensate for reduced local heat exchange efficiency in case of condensate accumulation) leads to a too high temperature in at least zones in the other tubes (tubes not having accumulated condensate on the shell side), i.e. causes hot spots in the stripper. This causes corrosion of the tubes (inner walls) by ammonium carbamate contained in the urea synthesis solution received in said tubes. The corrosion may occur localized in said hot spots. Hence, in the invention the risk of corrosion in the stripper tubes is reduced.

Generally, lifetime of an individual stripper tube is set by the minimum wall thickness so as to avoid the risk of tube rupture and of pinholes, and the risk of leakage or small leaks of corrosive medium into the shell space. A tube with a wall thickness below the safe minimum typically needs to plugged during a shutdown of the plant for maintenance. Tube plugging invariably introduces a significant point of risk of failure (in particular, the plug weld introduces a risk of leakage). Furthermore stripper maintenance frequency is set by the tubes in the tube bundle with the highest corrosion rate.

In preferred embodiments, segmental baffles and disc-and-donut baffles are (substantially) omitted in the present invention. It was surprisingly found with modelling studies that the heat exchange improves in this way. This is even more surprising because such baffles are used conventionally to improve heat transfer in shell-and-tube heat exchangers by providing cross-flow of the heating fluid. By omitting the baffles comprising baffle plates in the shell space, condensate accumulation is avoided in the shell space in the vertical zone where the tubes are of greater risk of corrosion. This corrosion risk zone is e.g. the zone above the level that is 10% of the effective tube length above the upper surface of the bottom tube sheet. Some condensate accumulation may still occur in the invention in the shell space on the bottom tube sheet; this does not affect the corrosion risk.

In the present invention, preferably a support structure for the tubes, such as a grid structure, is arranged in the shell space to prevent buckling of the tubes and/or prevent tube vibration.

As used herein, for process streams (in particular urea solution), high pressure (HP) is at least 100 bara, e.g. 110-160 bara, medium pressure (MP) is 20-60 bara, low pressure (LP) is 4-10 bara. These pressure ranges are for process solutions and not necessarily the same for heating fluids such as steam. The abbreviation "bara" means bar absolute.

The invention pertains in a first aspect to a method for stripping a urea synthesis solution. The urea synthesis solution is received from a urea forming process wherein ammonia and $CO_2$ are reacted under urea forming conditions. The urea synthesis solution is for instance received from a urea reaction section comprised in a high pressure section of a urea plant, which high pressure section furthermore comprises a high pressure carbamate condenser.

The invention in an aspect also pertains to a urea production process comprising: reacting $NH_3$ and $CO_2$ under urea-forming conditions in a reaction zone of a high pressure section of a urea plant to give urea synthesis solution, stripping the urea synthesis solution at high pressure in a stripper according to the invention, to give stripped urea solution and mixed gas, and condensing the mixed gas to form ammonium carbamate solution in a high pressure condenser, and supplying the ammonium carbamate solution from the high pressure condenser to the reaction zone. The urea production process is carried out in the inventive urea production plant comprising the inventive stripper as discussed.

The urea synthesis solution comprises urea, water and ammonium carbamate, free ammonia and some free $CO_2$. The urea synthesis solution is at high pressure in the stripper tubes, e.g. above 100 bar or above 140 bar. The urea solution at the stripper inlet is e.g. at least 180° C.

The method comprises subjecting the urea synthesis solution in the stripper tubes to stripping and to indirect heat exchange through the tube wall with the heat exchange fluid that is provided in the shell space of the stripper, whereby the heat exchange fluid condenses at least in part (such as for at least 80 wt. % or at least 90 wt. %) and transfers heat to the urea synthesis solution inside the tubes. The condensation occurs for a large part on the tube outer surfaces.

The tube wall temperature at the highest part of the effective tube length (just below the upper tube sheet) is e.g. at least 175° C., preferably in the range of 175-185° C. The highest tube wall temperature is for example reached in a vertical zone at 70-90% of the effective tube length from the top of the effective tube length (i.e. from the upper tube sheet bottom) and is e.g. at least 180° C., for instance 190-225° C.

The heat exchange fluid is preferably steam. The steam pressure is e.g. 15-30 bar and for instance saturated steam is used or steam with a temperature of up to 10° C. above the saturated steam temperature. The steam mass fraction at the shell outlet is e.g. 0-20% (relative to total outlet steam, i.e. including condensate), preferably 0.0-5%, this indicates sufficient condensation to ensure good heat transfer.

The stripper is a vertical shell-and-tube heat exchanger comprising a tube bundle, a shell and a shell space. The shell is for instance provided by a cylindrical vessel. The stripper also comprises an upper and lower tube sheet. The tube bundle comprises tubes, preferably straight tubes. In the method, the urea synthesis solution is provided as a falling film in the tubes and a heating fluid is supplied into the shell space. The shell space is the space within the shell, between the tube sheets, that is not occupied by the tubes. Hence, the shell space does not include the volume of the tube wall and the inner area of the tubes. In the event that a segmental baffle or disc-and-donut baffle is used, the baffle plate is arranged in the shell space. The stripper is configured as a falling film heat exchanger such that the tube bundle is arranged vertically. The tubes define the vertical axis of the stripper.

The method involves subjecting the urea synthesis solution to stripping. The stripping typically involves contacting the urea synthesis solution in the tubes in the stripper with a counter-current strip gas stream. The strip gas stream has a lower partial vapor pressure of $NH_3$ and/or $CO_2$ than the urea synthesis solution. The stripping is for instance $CO_2$ stripping, ammonia stripping or self-stripping. These types of stripping are known in the field for urea plants.

Accordingly the stripping involves e.g. $CO_2$ stripping using at least part of the feed $CO_2$ as strip gas that is supplied into the tubes at the bottom (wherein the $CO_2$ feed for instance comprises an amount of added passivation air, e.g. in an amount of 0.01-0.6 vol. % $O_2$ relative to $CO_2$ feed), or e.g. ammonia stripping using feed $NH_3$ supplied as strip gas into the tubes at the bottom.

The stripping can also involve e.g. self-stripping wherein the strip gas is effectively provided by heating of the urea synthesis solution in the stripper tubes, wherein the urea synthesis solution contains excess ammonia (e.g. N/C ratio more than 3) such that heating in the bottom parts of the stripper tubes gives relatively ammonia-rich gas. This gas passes upward through the stripper tubes and acts as strip gas for the falling film of urea synthesis solution in the upper parts of the tubes.

By the effect of heating and the strip gas, ammonium carbamate in the urea synthesis solution decomposes into $CO_2$ and $NH_3$ in the stripper tubes, which $CO_2$ and $NH_3$ are removed as gas from the liquid and leave the stripper at the top as mixed gas stream which is supplied at least in part to the high pressure carbamate condenser. The ammonium carbamate decomposition is endothermic.

Typically but not exclusively, the tube bundle has an effective tube length of 4 to 9 meters, e.g. 6-7 m, wherein the effective tube length is the length of the tube part that is in contact with steam. Hence, the effective tube length is the same as the vertical length of the shell space which is provided between the tube sheets.

The tube bundle has an outer tube limit (OTL) as is usual in the art. The outer tube limit is the circle created by encircling the outermost tubes in a tube bundle. The diameter of this circle is the OTL diameter.

Typically but not exclusively, the tube bundle has a ratio of the effective tube length to the outer tube limit diameter of the tube bundle which is 2.5 or less, e.g. 2.0 or less.

The tube bundle comprises for instance at least 1000 tubes, at least 2000 tubes, at least 3000 tubes or at least 4000 tubes or at least 5000 tubes, or even at least 8000 tubes, or even more tubes. For instance more than 4000 tubes can be used in a urea plant with a design capacity of about 3500 MTPD urea. Scale of economy for urea plants leads to ever larger scale urea plants with the limits mostly being set by construction and transport of the equipment such as the stripper. Hence the present invention can also be applied usefully with strippers with very high numbers of tubes such as e.g. 8000 to 10.000 tubes or even 10.000 to 20.000 tubes, for example. The OTL of the tube bundle may for instance be at least 2 m, at least 2.5 m, at least 3.0 m, or even at least 4.0 m. Tube spacing, tube wall thickness and tube internal diameter are generally independent of stripper capacity such that a stripper with more tubes usually has a larger OTL diameter and can have the same effective tube length.

The shell space preferably has a drainage area for steam condensate at each vertical level of the shell space. In some embodiments, the shell space has, at each vertical level where the tubes are contacted with steam, a drainage area for steam condensate. Preferably this contacting of the tubes with steam is carried out for at least some tubes (but not necessarily all tubes) at each vertical level of the shell space, the shell space terminating at the tube sheets. The drainage area as used herein is the empty area of the shell space suitable for drainage of condensate present on the shell side of the tubes. The drainage area hence excludes any occupied parts (such as by baffles) and also does not include the surface area occupied by the tubes (inner space and tube wall) because the tubes are not part of the shell space. The drainage area is hence also the flow area for steam. Accordingly, the shell space is preferably undivided in vertical direction for flow of steam and/or condensate.

The stripper contains an outlet for condensate arranged in a lower part of the shell space, e.g. provided in the shell directly above the bottom tube sheet.

The shell space preferably contains a vertical zone of at least 1.6 m vertical length which does not include baffles (in particular does not include segmental baffles, disc baffles or donut baffles) or substantially does not include baffles. Preferably, the shell space does not at all include segmental baffles or disc and donut baffles. In other embodiments wherein such baffles (segmental baffles or disc-and-donut baffles) are provided in the shell space, then each baffle is preferably vertically spaced apart from other baffles and the tube sheets by more than 1.6 m, more preferably more than 3 m. This applies in particular to baffles having a surface area (excluding the holes for the tubes) of more than 20% or more than 50% of the horizontal surface area of the shell space, as is typical for segmental baffles, donut baffles and disc baffles. Herein, 'horizontal' refers to the plane perpendicular to the tubes.

Typically but not exclusively the shell space comprises a continuous vertical zone of at least 1.6 m vertical length wherein for each horizontal cross section of said shell space in said vertical zone, the difference in drainage area between any two circular areas of at least 0.25 m², preferably of 0.25 to 0.50 m², which circular areas are of the same size (circles with same diameter), and which circular areas are both located within said outer tube limit, is less than 5% relative to the average drainage area of the two circular areas. Herein, 'horizontal' refers to the plane perpendicular to the tubes. The drainage area as used herein is the empty area of the shell space suitable for drainage of condensate present on the shell side of the tubes. As an example, the two circular areas each have a diameter of 0.60 m. In an embodiment, the continuous vertical zone is of 1.6 m to 3.0 m vertical length. In a preferred embodiment, the continuous vertical zone is of at least 3.0 m vertical length. In a preferred embodiment, the vertical length of the continuous vertical zone is at least 60%, at least 70%, at least 80% or even and most preferably at least 90% of the effective tube length. A longer or relatively longer continuous vertical zone advantageously provides for good heat transfer in the stripper.

Figure 1:
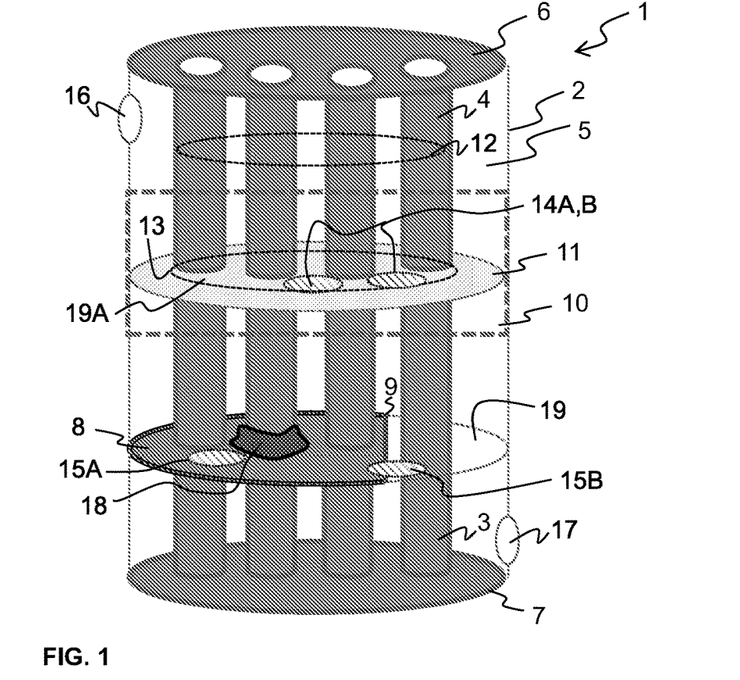
FIG. 1 schematically illustrates a stripper according to the invention.

As is schematically illustrated in FIG. 1, the stripper (1) (being an example shell-and-tube heat exchanger) comprises a shell (2) and a tube bundle (3), which comprises tubes (4) (only four tubes are shown, in practice typically more than 3000 tubes are provided). The stripper further comprises an upper tube sheet (6) and a bottom tube sheet (7). The space in the shell between the tube sheets that is not occupied by the tubes (neither by the tube wall nor the tube internal space) provides the shell space (5). The tube bundle has an outer tube limit (OTL) (12) which is the circle encircling the outer tubes. The shell (2) comprises an inlet (16) for gaseous heating fluid (e.g. steam) into the shell space (5) arranged at the top and an outlet (17) for condensate (and possibly some remaining steam) from the shell space at the bottom.

The stripper comprises a segmental baffle plate (8) for the purposes of illustration; the use of a segmental baffle plate is not preferred. The segmental baffle (8) has a cut-off (9) which provides open space (19) for flow of the steam and drainage of condensate in the shell space at the height of the baffle (8).

The shell space (5) furthermore includes a continuous vertical zone (10) which is free of segmental baffles and disc and donut baffles, or other structures which occupy a large horizontal area. For each horizontal cross section (11) of said continuous vertical zone (10), the outer tube limit (12) defines a region (13) of the cross section (11) that is within said outer tube limit (12). In this region (13), two circular areas (14A, 14B) can be defined of at least 0.25 m² and with identical diameter, and which are hence both located in the horizontal cross section and within the OTL. Preferably the two circular areas are 0.25-0.50 m². Preferably the two circular areas both have a diameter of 0.60 m.

It is noted that in the simplified drawing of FIG. 1, the circular areas (14,15) have a diameter of about 20% of the OTL diameter, e.g. circular areas of 0.60 m diameter and an OTL diameter of 3.0 m. However, the tubes (4) are magnified in diameter. In practice, any circular area of at least 0.25 m² in the OTL will encompass typically at least 20 tubes. For instance, in an example embodiment with tubes arranged in a hexagonal pattern and a center-to-center tube distance of e.g. about 40 mm, any circular area of at least 0.25 m² will encompass typically at least 100 tubes.

Taking into account that cross section (11) is not a plate and that the shell space is empty at said cross section, the drainage area is for both circular areas the same. Accordingly, the difference in drainage area between the two circular areas is 0%. The entire region (13) is empty space, allowing for drainage of condensate and hence provides for drainage area (19A) of the cross section (11).

In comparison, for a cross section at the height of segmental baffle (8), there will be at least two circular areas (of at least 0.25 m²) within the OTL boundary which have a difference in surface area of more than 5% relative to the average drainage area of the two circular areas. For instance, the circular area (15A) of 0.25 m$^2$ is located at the baffle 8 and has 0 m$^2$ drainage area whereas the second circular area (15B) also of 0.25 m$^2$ is in part located in the cut-off of the baffle and hence has a drainage area of e.g. 0.125 m$^2$, giving a difference in surface drainage area of 0.125 m$^2$ which is 200% of the average surface drainage area (of 0.0625 m$^2$), hence more than 5%. Hence, any vertical zone of the shell space including the illustrated segmental baffle (8) is not a continuous vertical zone wherein for each horizontal cross section of said shell space in said vertical zone, the difference in drainage area between any two circular areas of at least 0.25 m$^2$ located within said outer tube limit is less than 5% relative to the average drainage area of the two circular areas. As is illustrated, for baffle plate (8) there will be circular areas which are for the major part in the cut-off open space (19) and circular areas entirely on the baffle plate, the circular areas being at least 0.25 m$^2$, in particular if the OTL diameter is more than 2 m. For instance if the cut-off width is 60 cm and the OTL is 2 m or more, at least one circular area is entirely within the cut-off open space.

Furthermore, all circular areas of the appropriate size need to be compared that are within the OTL boundary. The continuous vertical zone (10) is only a selection of two height limits and not a limitation in the horizontal plane.

Furthermore in operation steam condenses (typically on the tubes where heat is withdrawn) and condensate (18) accumulates on the baffle plate (8), in particular in a horizontal zone far removed (e.g. more than 20 cm) from the cut-off (9). As said, baffle plate (8) is not preferred and preferably is entirely omitted.

If in FIG. 1 the vertical distance between baffle plate (8) and upper tube sheet (6) is more than 1.6 m, then stripper (1) includes a vertical zone as defined above.

In a preferred embodiment, the stripper comprises one or more support structures for supporting the tubes of the tube bundle, which support structure is arranged in the shell space. The support structure helps to avoid vibrations, especially during start-up and shut down. The support structure also helps to avoid buckling by reducing the unsupported length of the tubes. The support structure preferably comprises strips arranged in the horizontal plane between the tubes. The strips have for instance a width (minimum dimension in horizontal plane) of less than 10 mm, such as less than 6 mm. Steam condensate accumulation on the strips is hence avoided. The length of the strips (in horizontal plane) is e.g. more than 1.0 m. Strip height (vertically) is e.g. at least 5 mm, or at least 10 mm, e.g. in the range of 5-40 mm, such as 10-30 mm. The strips are e.g. arranged in a grid. Preferably the support structure comprises a mounting ring; the mounting ring is preferably circular. In some embodiments the mounting ring is provided with one vertical layer of strips. In other embodiments the mounting ring is provided with for instance at least 2 layers of strips with the strips in each layer (substantially) parallel to each other (e.g. 175°-180° angle) and wherein the strips have a different direction in adjacent layers and have crossing points. Preferably the strips of adjacent layers are above each other at least at the crossing points. Preferably the strips in one layer do not cross each other. The angle between the strips in adjacent layers typically matches the tube pitch (e.g. triangular pitch) in the tube bundle so as to hold the tubes in place. The strips in adjacent layers of a mounting ring are preferably joined to each other, at some but typically not all of the crossing points. The strips can also be interlocking. The joining or interlocking of strips of different layers of strips attached to the same mounting ring provides a sturdy grid which reduces the risk of any vibrations of the tubes. The support structure is located between the upper and lower tube sheet in vertical direction. The support structure is arranged horizontally.

The strips do not need to be straight (in horizontal plane); they can for instance also be curved to bend around the tubes. Strips in the same layer are spaced apart from each other in horizontal direction by the stripper tubes and hence by (about) the tube outer diameter. The stripper can include a plurality of the support structures which vertically spaced apart.

Preferably the support structures have an occupied surface area of less than 70%, or less than 50%, or less than 30% of the shell space surface area in the OTL in horizontal cross-section (wherein the shell space surface area does not include the surface area occupied by the tubes).

Figure 2:
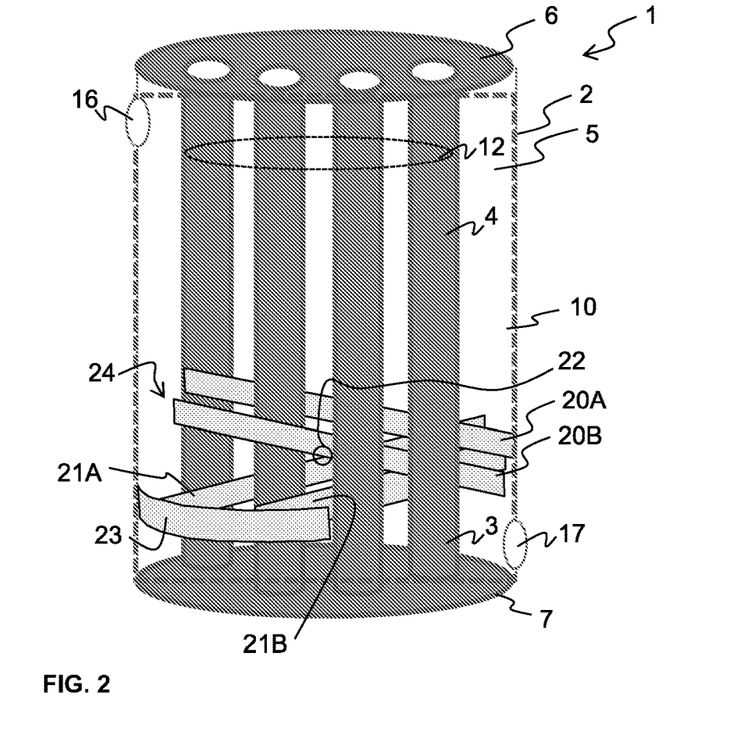
FIG. 2 schematically illustrates a stripper according to the invention.

FIG. 2 schematically illustrates an example inventive stripper with an example of such a grid. The stripper (1) is overall as illustrated in FIG. 1, except that segmental baffle plate (8) is omitted. In the shell space (5) a support structure (24) is provided which comprises a number of parallel strips (20A,20B) in a first layer and a number of parallel strips (21A, 21B) in a second layer which is vertically below the first layer of strips. The strips (20A, 20B) of the first layer and the strips of the second layer (21A, 21B) are both vertical strips extending between the tubes; the tubes are typically arranged in rows in the tube bundle. The strips of the first and second layer are at an angle to each other and have crossing points. The crossing point (22) of strips (21A and 20B) is illustrated with a circle; the strips are e.g. joined or connected at this crossing point. The stripper furthermore comprises a circular mounting ring (23), illustrated in part, to which the strips (21A, 21B) of the second layer are mounted, e.g. joined. The support structure (24) is open enough so as to not interrupt the continuous vertical zone (10) (dashed line). The continuous vertical zone (10) in this example extends over the entire effective tube length, i.e. from the bottom of upper tube sheet (6) to top of bottom tube sheet (7). In operation some condensate may accumulate in the shell space (5) on the bottom tube sheet (7). This does not affect heat transfer by the heating fluid or the corrosion in the tubes.

Figure 3:
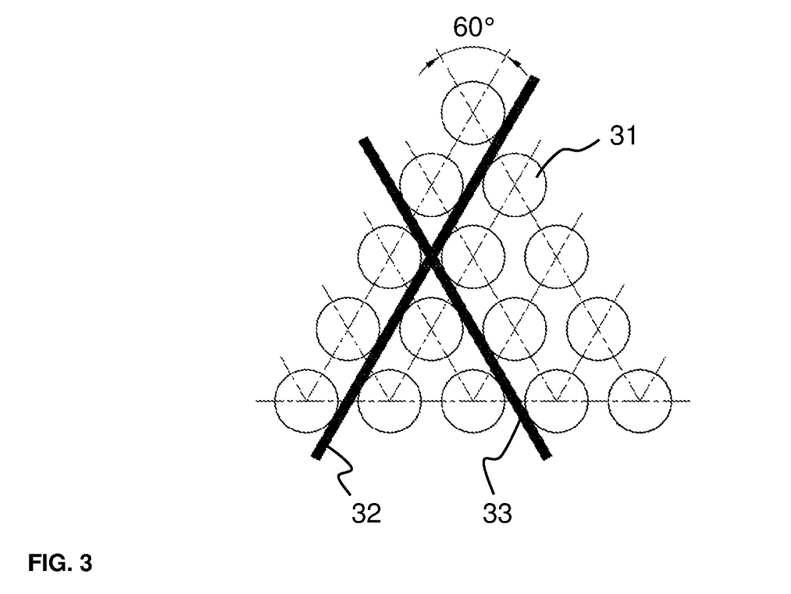
FIG. 3 schematically illustrates a support structure of a stripper according to the invention.

FIG. 3 schematically illustrates a view in vertical direction of a segment of a tube bundle. The tube bundle comprises stripper tubes (31) with a triangular pitch, i.e. 60° pitch. Two strips (32, 32) are arranged between the tubes as example support structure. The two strips are at an angle to each other and are at different layers in vertical direction. Each illustrated strip represents many strips parallel in the horizontal plane.

The invention also pertains to a striper as described, and to a urea plant comprising such a stripper.

Figure 4:
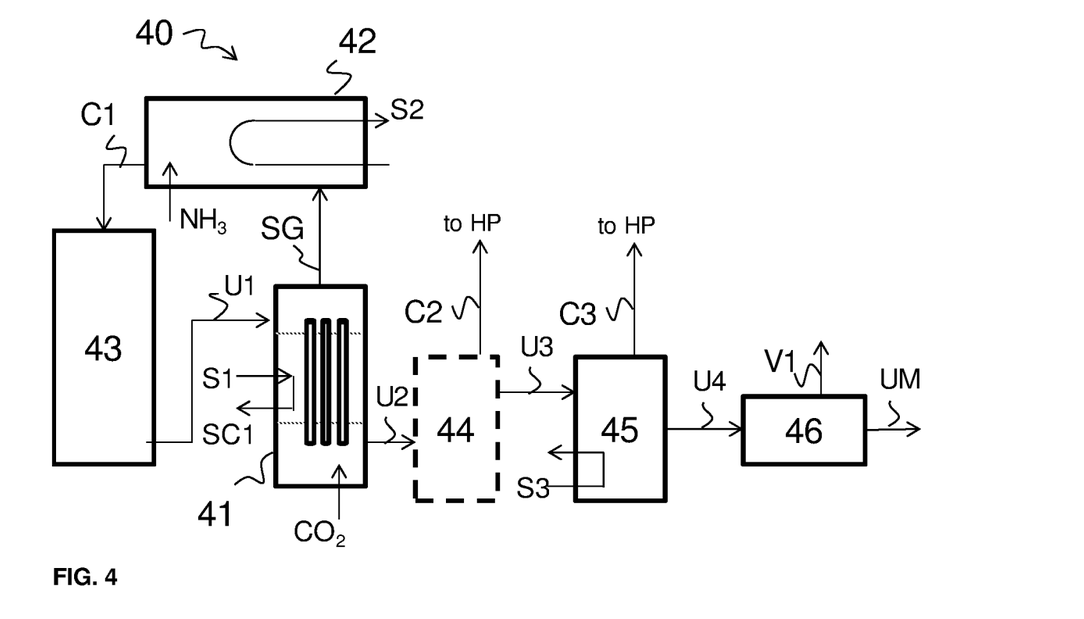
FIG. 4 schematically illustrates a urea plant according to the invention.

FIG. 4 schematically illustrates an example urea plant according to the invention. The urea plant (40) of the invention, comprises high pressure (HP) section comprising a stripper (41) according to the invention, with tubes and a shell space, a high pressure carbamate condenser (42), a reaction section (43), preferably a vertical urea reactor, an inlet for $CO_2$ feed and an inlet for $NH_3$ feed. The reaction section, stripper and high pressure carbamate condenser are connected so as to form a substantially isobaric loop. The reaction section (43) has an outlet for urea synthesis solution (U1) also comprising carbamate connected with an inlet of the stripper (41), which is for example a $CO_2$ stripper having an inlet for at least part of the $CO_2$ feed that is used as strip gas, wherein the $CO_2$ strip gas inlet is connected to a high pressure CO$_2$ compressor and is connected to the bottom openings of the tubes. The stripper has an outlet for mixed gas (SG) and an outlet for stripped urea solution (U2). The gas (SG) is supplied to a high pressure carbamate condenser (42) which is a shell-and-tube heat exchanger where the gas is condensed (either in the shell space or in the tubes) to carbamate solution (C1) which is supplied to the reactor (43). The carbamate condenser (42) may for instance have an inlet for NH$_3$ feed. The reactor and high pressure carbamate condenser are in some embodiments combined in a single vessel including a reaction section and a condensation section, for example in case of a pool reactor.

The stripper is as discussed and uses a condensable heating fluid (S1) (e.g. steam) in the shell space. The heating fluid (S1) is supplied at the top and condenses in the shell space to give condensate (SC1) withdrawn at the bottom. In the high pressure carbamate condenser, for instance steam (S2) is raised; for instance in the tubes. The urea plant optionally comprises a medium pressure recovery section (44) to which stripped urea solution (U2) is supplied and which comprises for instance a decomposer or a flash vessel to give a urea solution (U3) and a gas, and a condenser for said gas to give carbamate solution (C2) which is directly or indirectly recycled to the HP section. The plant further frequently comprises a low pressure recovery section (45) having an inlet for stripped urea solution (U2), optionally from said medium pressure processing, and comprising a decomposer using heating (e.g. with steam (S3)) to give purified urea solution (U4) and a gas, and a condenser for said gas to give carbamate solution (C3) which is recycled directly or indirectly to the HP section. The plant optionally further comprises an evaporation section (46), comprising for instance a vacuum evaporator, configured receiving purified urea solution (U4) and water evaporation to give a urea melt (UM) and vapor (V1). The plant optionally comprises a urea finishing section for solidifying the urea melt into solid urea product, e.g. a granulator or prilling tower.

The present invention also pertains to a shell-and-tube heat exchanger, preferably a vertical shell-and-tube heat exchanger, comprising a tube bundle comprising tubes, an upper and lower tube sheet and a shell, and a shell space provided in the shell between the upper and lower tube sheet, wherein the heat exchanger is configured for operation with a falling film of a liquid in the tubes, and wherein the tubes are for example made of a urea-grade corrosion resistance material, e.g. comprise for instance a duplex stainless steel, or are for instance bimetallic tubes, and wherein the tube sheets for instance contain a carbon steel plate with preferably a lining and/or overlay welding of preferably duplex stainless steel on the side that is in operation exposed to the liquid received in the tubes, and wherein the heat exchanger comprises an inlet for heating fluid to the shell space and an outlet for heating fluid from the shell space, wherein the inlet for heating fluid is arranged higher than the outlet for condensate from the shell space, wherein preferably liquid dividers are mounted on the upper end of the tubes, wherein the liquid dividers are sleeves or ferrules with for instance radial or tangential holes for entry of the liquid into the tubes; furthermore preferably having the same preferred and typical features as the stripper as discussed. Preferably the tubes of the tube bundle are supported by strips having a width of less than 10 mm. The heat exchanger is preferably a stripper according to the invention, or a stripper as used in the stripping method according to the invention.

The present invention pertains also to a stripper for a urea plant, preferably having the same features as said shell-and-tube heat exchanger, and preferably having the same preferred features as for the stripper used in the stripping method according to the invention.

The shell- and tube heat exchanger and the stripper furthermore may have the preferred features as discussed hereinafter.

The vertical shell-and-tube heat exchanger, preferably the stripper, is configured for operation with a falling film of a liquid in the tubes, such as urea synthesis solution to be stripped in the tubes, and heating fluid, such as steam, in the shell space. The heat exchanger, preferably stripper, comprises a tube bundle comprising tubes, an upper and lower tube sheet and a shell, and a shell space, wherein the shell space is preferably as discussed hereinabove. The tubes comprise for instance a ferritic-austenitic duplex stainless steel, e.g. a steel alloy as discussed in WO 95/00674, WO 2017/013180 and WO 2017/014632. Other kinds of urea grade steel are also possible. The tubes can for instance also comprise Ti or Zr. The tubes are for instance bimetallic tubes with for instance a Zr inner layer, for example in case the heat exchanger is a stripper of the self-stripping type. The tube wall thickness is e.g. 1.0 to 5 mm, preferably 1.8-3.0 mm (design thickness). The tubes have a concave internal wall surface. Preferably the entirely concave internal wall surface of the tubes is made of duplex stainless steel or Zr. The tubes are preferably stripper tubes. The tube sheets typically contain a carbon steel plate with preferably a lining and/or overlay welding of urea grade steel, such as duplex stainless steel on the side of the tube sheet that is in operation exposed to the liquid received in the tubes, e.g. the sides exposed to urea solution.

The heat exchanger comprises an inlet and an outlet for heating fluid, such as steam, to and from the shell space, wherein the inlet is typically arranged higher than the outlet for condensate from the shell space. The heat exchanger, preferably a stripper for a urea plant, is for example configured for co-current downward flow of liquid in the tubes and heating fluid in the shell space. The heat exchanger, preferably stripper, has an inlet for liquid (such as urea synthesis solution or ammonium carbamate solution) at the top, an outlet for heated liquid (such as stripped urea solution) at the bottom and an outlet for mixed gas at the top. Optionally the heat exchanger (preferably stripper) comprises an inlet for strip gas, such as CO$_2$, at the bottom connected, preferably for introducing at least a part of the CO$_2$ feed into the tubes as strip gas. The tubes extend for example through the upper tube sheet and are for instance welded to the upper side of the upper tube sheet.

Typically but not exclusively, liquid dividers are mounted on the upper end of the tubes. The liquid dividers are for instance sleeves or ferrules with holes, for entry of the liquid into the tubes. The holes are for instance tangential or radial holes in the walls of the liquid dividers, e.g. in the sleeves or ferrules. The liquid dividers are configured to provide a falling film of liquid (preferably urea synthesis solution to be stripped) on the internal walls of the tubes in operation.

One liquid divider is mounted on or into one tube at the upper end. As the tubes typically protrude through the upper tube sheet, the upper tube end is arranged above the upper surface of the upper tube sheets. The liquid dividers are positioned on protruding tube ends of the tubes, and are often provided with a gas tube on top. Background references on the liquid dividers and strippers of urea plants including comprising such liquid dividers, are e.g. US 2012/0282149 and US 2012/0097378, in particular FIG. 2. The gas tube is for instance unitary with the liquid divider.

For instance each liquid divider has 3-5 holes, such as radial or tangential holes, preferably radial, of 2-5 mm diameter in the tube walls. The precise diameter of the holes is important to ensure good liquid film formation in the tubes. For the purposes of maintenance and inspection, including for tube plugging, it is desirable that the liquid dividers can be removed. Hence, the tube-to-tube sheet joints do not go through the liquid dividers or sleeves. The liquid dividers and gas tubes are kept in place e.g. by a locking plate or grid arranged on top of the gas tubes. The gas tubes and liquid dividers are typically not welded to the upper tube sheet. A liquid divider is typically not welded to the tubes.

The heat exchanger, preferably striper, preferably comprises an upper chamber. The upper chamber has as bottom the upper side of the upper tube sheet, side walls provided by the vessel of the heat exchanger, an inlet opening for liquid (urea synthesis solution) and an outlet for gas. Preferably the upper chamber further comprises a feed pipe.

The heat exchanger, preferably the stripper, typically but not exclusively contains in the shell space a continuous vertical zone of at least 1.6 m or at least 3.0 m vertical length which zone preferably contains no baffles and/or preferably wherein for each horizontal cross section of said shell space in said vertical zone, the difference in drainage area between any two circular areas of at least 0.25 m$^2$ located in said horizontal cross section within said outer tube limit is less than 5% relative to the average drainage area of the two circular areas; with further preferences of continuous vertical zone as discussed in connection with the method.

The heat exchanger, preferably stripper, preferably comprises a support structure as discussed hereinabove. It is noted that segmental baffles as used in the prior art in principle have many holes but these are almost fully occupied by the tubes, such that the segmental baffle plate provides a rather large horizontal plate in the shell space on which condensate may accumulate. For instance for a tube in the centre of the tube bundle with 1.5 m OTL diameter, the distance to the cut-off may be more than 0.30 m, which would be the minimum horizontal distance for condensate formed in the tube bundle center to a drainage point. By instead using the preferred strips of e.g. 5 mm width, the horizontal drainage distance is significantly reduced.

Accordingly, preferably the shell space comprises, more preferably comprises only, structures having a maximum horizontal drainage distance of less than 10 mm or less than 5 mm for any point on the horizontal surface that is less than 5 cm removed in horizontal direction from an outer surface of a stripper tube of the tube bundle, wherein the horizontal drainage distance is the distance over the horizontal surface between that point and a drainage point allowing for drainage of condensate. The drainage point is for instance an opening in the structure which is not occupied by a tube or a clearance between the structure and the shell.

The invention also pertains to a method of modifying an existing urea plant (a so-called revamping method). The existing urea plant is a urea plant comprising an existing high pressure stripper. The existing stripper is configured as vertical falling film shell-and-tube heat exchanger and comprises a tube bundle comprising tubes, a shell, and an upper and lower tube sheet, and a shell space provided in the shell between the upper and lower tube sheet. The existing stripper is adapted for maintaining a falling film of urea synthesis solution to be stripped in the tubes and comprises an inlet for steam supplied to the shell space and an outlet for steam and condensate from the shell space. The existing stripper comprises in the shell space baffles, such as segmental baffles, or disc and donut baffles. The method of modifying the plant comprises a step of removing at least some, preferably all of the baffles in the shell space of the stripper, in particular removing some, preferably all of the segmental baffles and/or disc and donut baffles provided in the existing stripper, and preferably a step of installing in the stripper shell space one or more support structures as described above, wherein the support structure preferably comprises strips and/or a grid structure as described. Preferably 2 to 6 support structures of the said type are installed. Preferably by the revamping method a continuous vertical zone as described is formed in the stripper, for instance a continuous vertical zone of at least 1.6 m or at least 1.9 m or at least 3.0 m vertical length, wherein for each horizontal cross section of said shell space in said vertical zone, the difference in drainage area between any two circular areas of at least 0.25 m$^2$ which have the same size and which are located in said horizontal cross section within said outer tube limit is less than 5% relative to the average drainage area of the two circular areas.

The stripping method is carried out in the inventive stripper as discussed and preferably in the urea plant as discussed. The urea production process comprises as a step the stripping method in the inventive stripper. The urea production process is preferably carried out in the urea plant according to the invention. Preferences for the stripper design discussed in connection with the stripping method apply equally to the inventive stripper and the stripper of the inventive urea plant, and vice versa. The inventive revamping method preferably gives a urea plant according to the invention and/or a urea plant comprising a stripper according to the invention. Preferences for the stripper design that are discussed in connection with the stripping method, the inventive stripper and the stripper of the inventive urea plant, apply equally to the modified urea plant of the revamping method. Preferences for the stripper design described in connection with the stripping method or the inventive stripper apply equally to the shell-and-tube heat exchanger. Preferences mentioned for the shell-and-tube apply equally to the stripper used in the inventive stripping method and the inventive stripper.

As used herein, the term "typically" indicates features which are advantageous but not mandatory for the invention described.

The present application also pertains to a high pressure stripper for a urea plant configured as vertical falling film shell-and-tube heat exchanger and comprising a tube bundle comprising tubes, a shell, and an upper and lower tube sheet, and a shell space provided in the shell between the upper and lower tube sheet, wherein the stripper is adapted for maintaining a falling film of urea synthesis solution to be stripped in the tubes and comprises an inlet for steam supplied to the shell space and an outlet for steam and condensate from the shell space, comprising baffles, such as segment baffles, disc baffles or donut baffles, wherein said baffles are inclined vertically so as to have a higher point and a lower point, the lower point allowing for drainage of condensate.

The inclination helps to prevent condensate accumulation and thereby reduces corrosion of the stripper tubes. The inclination angle is e.g. 5° to 45° from horizontal. Compared to the stripper discussed above, inclined baffles have as disadvantage that it is difficult to mount the tube bundle through an inclined baffle. The provision of the bore holes in the baffle is also complex for inclined baffles. The application also pertains to a urea plant comprising such a stripper with inclined baffle plates, a urea production process carried out in such a urea plant, and a stripping method carried out in such a stripper, with the preferred features described as hereinabove except for the continuous vertical zone.

The present application also pertains to a high pressure stripper for a urea plant configured as vertical falling film shell-and-tube heat exchanger and comprising a tube bundle comprising tubes, a shell, and an upper and lower tube sheet, and a shell space provided in the shell between the upper and lower tube sheet, wherein the stripper is adapted for maintaining a falling film of urea synthesis solution to be stripped in the tubes and comprises an inlet for steam supplied to the shell space and an outlet for steam and condensate from the shell space, wherein the stripper comprises baffles comprising baffle plates, such as segment baffles, disc baffles or donut baffles. At least one of said baffles comprises a baffle plate with at least 2, preferably at least 10 holes through which no stripper tubes extend.

In this way the opening in the baffle plate provide drainage openings for condensate in the shell space. The baffles that are vertically spaced apart in the stripper have such drainage openings at corresponding positions in horizontal cross-section. The tubes sheets are closed (i.e. have no hole) at these horizontal positions and have a lining or overlay weld at these positions at the side exposed to the urea solution. In this way the carbon steel in the tube sheets is not exposed to corrosive medium. The condensate drainage openings provide the advantage that condensate accumulation in the shell space is avoided and corrosion is reduced. Compared to the stripper with a continuous vertical zone, the stripper with baffles with holes has the disadvantage that for a given number of tubes, the size of the stripper increases because part of the volume within OTL is used for these drainage openings. The drainage openings in a baffle plate are preferably spaced apart in horizontal direction, e.g. with at least 5 or at least 10 tubes between two drainage openings that are arranged in the same line of the tube pitch.

The application also pertains to a urea plant comprising such a stripper with baffle plates comprising holes for drainage of condensate, a urea production process carried out in such a urea plant, and a stripping method carried out in such a stripper, with the preferred features described as hereinabove except for the continuous vertical zone.

The stripper efficiency (alfa) is used herein is calculated as the amount of ammonia converted to urea (and biuret) divided by the total amount of ammonia, typically measured at the liquid outlet of the stripper. Hence, alfa=(2*wt. % urea/60)/((2*wt. % urea/60)+(wt. % $NH_3$/17)), measured at the liquid outlet of the stripper, wherein wt. % $NH_3$ includes all ammonia species including ammonium carbamate.

Example 1

En example embodiment of the invention will now be further illustrated by the following Example, which does not limit the invention and which does not limit the claims.

An existing urea plant with a high pressure $CO_2$ stripper with 3000 to 5000 stripper tubes and 5 donut baffles and 4 disc baffles (in alternating pattern) in the shell space, and comprising a tube bundle with an effective tube length of 6.0 m and OTL diameter of 2.5-3.0 m, was modified by removing all the donut baffles and all the disc baffles and installing instead a number of support structures (e.g. 4 to 6 support structures). The support structures are sufficiently open to not interrupt a continuous vertical zone as defined above. In particular the support structures each comprise a mounting ring and strips. The strips have e.g. 3 mm width and 20 mm height. By the modification, the stripper contains a continuous vertical zone as discussed and the heat transfer in the stripper is improved and cold spots of the tubes are avoided. With a fixed stripping efficiency (alfa), the steam temperature and pressure were reduced by the modification and accordingly there were fewer tubes with a too high corrosion rate. With the modification, any corrosion that may occur preferentially in some of the tubes, for example in the tubes arranged in outer ring of the tube bundle and less in the tubes in the centre of the tube bundle, is reduced or even completely avoided.

The invention claimed is:

1. A method for stripping a urea synthesis solution received from a urea forming process wherein ammonia and $CO_2$ are reacted under urea forming conditions, wherein the urea synthesis solution comprises urea, water and ammonium carbamate, the method comprising:
   subjecting the urea synthesis solution to stripping and indirect heat exchange with a gaseous heating fluid in a stripper, wherein the stripper is a vertical shell-and-tube heat exchanger comprising a tube bundle comprising tubes, a shell and a shell space, wherein the urea synthesis solution is provided as falling film in the tubes and wherein the heating fluid is supplied in the shell space and condenses at least in part in the shell space,
   wherein the tube bundle has an effective tube length of 4 to 9 m, wherein each tube of said tubes comprises a tube part that is in contact with the heating fluid, wherein the effective tube length is the length of said tube part that is in contact with the heating fluid,
   wherein the tube bundle has an outer tube limit and a ratio of the effective tube length to the outer tube limit diameter that is 2.5 or less, wherein the outer tube limit is the diameter of the circle created by encircling the outermost tubes in the tube bundle,
   wherein the shell space has, at each vertical level where the tubes are contacted with heating fluid, a drainage area for heating fluid condensate, the drainage area being the empty area of the shell space suitable for drainage of condensate present on the shell side of the tubes,
   wherein said shell space comprises a continuous vertical zone of at least 1.6 m vertical length, wherein:
   (i) in said continuous vertical zone for each horizontal cross section along the plane perpendicular to the tubes of said shell space, the difference in drainage area between any two circular areas of at least 0.25 $m^2$ which have the same size and which are located in a region in said horizontal cross section and within said outer tube limit is less than 5% relative to the average drainage area of the two circular areas, and/or
   (ii) wherein said continuous vertical zone does not include baffles.

2. The method according to claim 1, wherein said continuous vertical zone does not include baffles.

3. The method according to claim 1, wherein the tubes are supported by strips having a width of less than 10 mm.

4. The method according to claim 1, wherein the continuous vertical zone has a vertical length that is at least 90% of the effective tube length.

5. The method according to claim 1, wherein the stripping is $CO_2$ stripping, ammonia stripping, or self-stripping.

6. The method according to claim 1, wherein the two circular areas both have a diameter of 0.60 m.

7. A urea plant comprising a high pressure synthesis section comprising a urea reaction section, a high pressure carbamate condenser and a stripper, wherein the stripper is configured as vertical falling film shell-and-tube heat exchanger and comprises a tube bundle comprising tubes, a shell, and an upper tube sheet and a lower tube sheet, and a shell space provided in the shell between the upper tube sheet and the lower tube sheet, wherein the stripper is adapted for maintaining a falling film of urea synthesis solution to be stripped in the tubes and comprises an inlet for gaseous heating fluid supplied to the shell space and an outlet for gaseous heating fluid and heating fluid condensate from the shell space, wherein the tube bundle has an effective tube length of 4 to 9 m, wherein each tube of said tubes comprises a tube part that is in contact with the heating fluid, wherein the effective tube length is the length of said tube part that is in operation of the plant in contact with the heating fluid, wherein the tube bundle has an outer tube limit and a ratio of the effective tube length to the outer tube limit diameter that is 2.5 or less, wherein the outer tube limit is diameter of the circle created by encircling the outermost tubes in the tube bundle, wherein the shell space has, at each vertical level where the tubes are contacted with the heating fluid, a drainage area for heating fluid condensate, the drainage area being the empty area of the shell space suitable for drainage of condensate present on the shell side of the tubes, wherein said shell space comprises a continuous vertical zone of at least 1.6 m vertical length wherein (i) in said continuous vertical zone for each horizontal cross section along the plane perpendicular to the tubes of said shell space in said vertical zone, the difference in drainage area between any two circular areas of at least 0.25 m$^2$ which have the same size and which are located in said horizontal cross section within said outer tube limit is less than 5% relative to the average drainage area of the two circular areas and/or (ii) wherein said continuous vertical zone does not include baffles.

8. A urea plant according to claim 7, wherein the urea plant further comprises a $CO_2$ compressor, and wherein the stripper furthermore comprises an inlet for $CO_2$ feed from the $CO_2$ compressor to the bottom ends of the tubes of the stripper.

9. A urea plant according to claim 7, wherein the tubes have internal walls, wherein liquid dividers are mounted on upper ends of the tubes, which upper ends extend through the upper tube sheet, and wherein the liquid dividers are sleeves or ferrules with holes for liquid entry configured to provide a falling film of urea synthesis solution on the internal walls of the tubes in operation.

10. A urea plant according to claim 7, wherein the tubes are supported by strips having a width of less than 10 mm.

11. A urea plant according to claim 7, wherein the stripper comprises a support structure arranged in the shell space for supporting the tubes, wherein the support structure comprises a circular mounting ring with at least one layer of strips, wherein the strips are connected to the mounting ring.

12. A urea plant according to claim 11, wherein the mounting ring comprises at least two layers of strips arranged on top of each other, with the strips in each layer arranged parallel to each other and wherein the strips in adjacent layers cross each other so as to have crossing points.

13. A method for stripping a urea synthesis solution received from a urea forming process wherein ammonia and $CO_2$ are reacted under urea forming conditions, wherein the urea synthesis solution comprises urea, water and ammonium carbamate, the method comprising:

subjecting the urea synthesis solution to stripping and indirect heat exchange with a gaseous heating fluid in a stripper, wherein the stripper is a vertical shell-and-tube heat exchanger comprising a tube bundle comprising tubes, a shell and a shell space, wherein the urea synthesis solution is provided as falling film in the tubes and wherein the heating fluid is supplied in the shell space and condenses at least in part in the shell space, wherein the tube bundle has an effective tube length of 4 to 9 m, wherein each tube of said tubes comprises a tube part that is in contact with the heating fluid, wherein the effective tube length is the length of said tube part that is in contact with the heating fluid, wherein tubes are supported by strips having a width of less than 10 mm.

14. A high pressure stripper for a urea plant comprising a vertical shell-and-tube heat exchanger comprising a tube bundle comprising tubes, a shell, and an upper tube sheet and lower tube sheet, and a shell space provided in the shell between the upper and lower tube sheet, wherein the stripper is adapted for maintaining a falling film of urea synthesis solution to be stripped in the tubes and comprises an inlet for gaseous heating fluid supplied to the shell space and an outlet for gaseous heating fluid and heating fluid condensate from the shell space, wherein the inlet for heating fluid is arranged higher than the outlet for condensate from the shell space, wherein the tubes of the tube bundle are supported by strips having a width of less than 10 mm.

15. The stripper of claim 14, wherein the stripper comprises liquid dividers which are mounted on the upper end of the tubes, and wherein the liquid dividers are sleeves or ferrules which comprise radial or tangential holes for entry of the liquid into the tubes.

16. The stripper of claim 14, wherein the tube sheets contain a lining or overlay welding of duplex stainless steel on the side of the tube sheet that is in operation exposed to the liquid received in the tubes.

17. A high pressure stripper for a urea plant comprising a vertical falling film shell-and-tube heat exchanger which comprises a tube bundle comprising tubes, a shell, and an upper tube sheet and a lower tube sheet, and a shell space provided in the shell between the upper tube sheet and the lower tube sheet, wherein the stripper is adapted for maintaining a falling film of urea synthesis solution to be stripped in the tubes and comprises an inlet for gaseous heating fluid supplied to the shell space and an outlet for gaseous heating fluid and heating fluid condensate from the shell space, wherein the tube bundle has an effective tube length of 4 to 9 m, wherein each tube of said tubes comprises a tube part that is in contact with the heating fluid, wherein the effective tube length is the length of said tube part that is in operation of the plant in contact with the heating fluid, wherein the tube bundle has an outer tube limit and a ratio of the effective tube length to the outer tube limit diameter that is 2.5 or less, wherein the outer tube limit is diameter of the circle created by encircling the outermost tubes in the tube bundle, wherein the shell space has, at each vertical level where the tubes are contacted with the heating fluid, a drainage area for heating fluid condensate, the drainage area being the empty area of the shell space suitable for drainage of condensate present on the shell side of the tubes, wherein said shell space comprises a continuous vertical zone of at least 1.6 m vertical length wherein (i) in said continuous vertical zone for each horizontal cross section along the plane perpendicular to the tubes of said shell space in said vertical zone, the difference in drainage area between any two circular areas of at least 0.25 m$^2$ which have the same size and which are located in said horizontal cross section within said outer tube limit is less than 5% relative to the average drainage area of the two circular areas and/or (ii) wherein said continuous vertical zone does not include baffles.

18. The stripper of claim 17, wherein the stripper comprises liquid dividers which are mounted on the upper end of the tubes, wherein the liquid dividers are sleeves or ferrules which comprise radial or tangential holes for entry of the liquid into the tubes.

19. The stripper of claim 17, wherein the tube sheets contain a lining or overlay welding of duplex stainless steel on the side of the tube sheet that is in operation exposed to the liquid received in the tubes.

20. A urea plant comprising a high pressure synthesis section comprising a urea reaction section, a high pressure carbamate condenser and a stripper, wherein the stripper is configured as vertical falling film shell-and-tube heat exchanger and comprises a tube bundle comprising tubes, a shell, and an upper tube sheet and a lower tube sheet, and a shell space provided in the shell between the upper tube sheet and the lower tube sheet, wherein the stripper is adapted for maintaining a falling film of urea synthesis solution to be stripped in the tubes and comprises an inlet for gaseous heating fluid supplied to the shell space and an outlet for gaseous heating fluid and heating fluid condensate from the shell space, wherein the tube bundle has an effective tube length of 4 to 9 m, wherein each tube of said tubes comprises a tube part that is in contact with the heating fluid, wherein the effective tube length is the length of tube part that is in operation of the plant in contact with the heating fluid, wherein the tube bundle has an outer tube limit and a ratio of the effective tube length to the outer tube limit diameter that is 2.5 or less, wherein the outer tube limit is diameter of the circle created by encircling the outermost tubes in the tube bundle, wherein the tubes are supported by strips having a width of less than 10 mm.

* * * * *